United States Patent [19]

Haubensak

[11] Patent Number: 5,602,329
[45] Date of Patent: Feb. 11, 1997

[54] METHOD AND APPARATUS FOR MEASURING FRACTURE TOUGHNESS OF A MATERIAL

[75] Inventor: Frederick G. Haubensak, Redwood City, Calif.

[73] Assignee: Massachusetts Institute of Technology, Cambridge, Mass.

[21] Appl. No.: 513,091

[22] Filed: Aug. 9, 1995

[51] Int. Cl.$^6$ .................................................. G01N 3/42
[52] U.S. Cl. ........................................ 73/82; 73/105
[58] Field of Search ............................. 73/82, 83, 85, 73/105, 821, 826, 834

[56] References Cited

U.S. PATENT DOCUMENTS

| | | | |
|---|---|---|---|
| 4,852,397 | 8/1989 | Haggag | 73/82 |
| 5,284,049 | 2/1994 | Fukumoto | 73/82 |

OTHER PUBLICATIONS

Smith et al., "Crack–Shape Effects for Indentation Fracture Toughness Measurements", J. Am. Ceram. Soc., 75 (1992) 305–315 Month unavailable.

Ramachandran et al., "Prediction of indentation–load dependence of fracture strengths from R–curves of toughened ceramics", Journal of Materials Science, 28 (1993) 6120–6126 Month unavailable.

Marion, "Use of Indentation Fracture to Determine Fracture Toughness", *Fracture Mechanics Applied to Brittle Materials, ASTM STP* 678, S. W. Freiman, Ed., American Society for Testing and Materials, 1979, pp. 103–111.

Ghosh et al., "Vickers Microindentation Toughness of a Sintered SiC in the Median–Crack Regime", Battelle Pacific Northwest Laboratories Report No. DE920000225/XAB Government Research Announcements and Index, 1991, pp. 1–33 Month unavailable.

Anstis et al., "A Critical Evaluation of Indentation Techniques for Measuring Fracture Toughness: I, Direct Crack Measurements", J. Am. Ceram. Soc., 64 (1981) 533–538 Sep.

Li et al., "Indentation Fracture Toughness of Sintered Silicon Carbide in the Palmqvist Crack Regime", J. Am. Ceram. Soc., 72 (1989) 904–911 Month unavilable.

Merkel et al., "Fracture toughness of sintered SiC ceramics: a comparison between different methods", Materials Science and Engineering, A151 (1992) 131–135 Month unavailable.

Lawn et al., "Elastic/Plastic Indentation Damage in Ceramics: The Median/Radial Crack System", J. Am. Ceram. Soc., 63 (1980) 574–580 Month unavailable.

Cook et al., "Direct Observation and Analysis of Indentation Cracking in Glasses and Ceramics", J. Am. Ceram. Soc., 73 (1990) 787–817 Month unavailable.

Evans et al., "Fracture Toughness Determinations by Indentation", J. Am. Ceram. Soc., 59 (1976) 371–372 Jul.

Lawn et al., "Microfracture beneath point indentations in brittle solids", Journal of Materials Science, 10 (1975) 113–122 Month unavailable.

Jurgen Rodel, James F. Kelly, Mark R. Stoudt, and Stephen J. Bennison; A loading device for fracture testing of compact tension specimens in the scnning electron microscope, Scanning Microscopy, 5, 29–35 Month unavailable 1991.

Crack–Shape Effects for Indentation Fracture Toughness Measurements, J. Am. Ceram. Soc., 75, 305–315, (1992) Smith et al. Month unavailable.

*Primary Examiner*—Richard Chilcot
*Assistant Examiner*—Ronald Biegel
*Attorney, Agent, or Firm*—Florence Fusco McCann

[57] ABSTRACT

A method is provided for determining the fracture toughness of a material based upon observation of crack opening displacement (COD) as a function of distance from the tip of a crack generated in the material. An apparatus is also provided for generating a crack in a material for subsequent fracture toughness determination.

29 Claims, 5 Drawing Sheets

METHOD AND APPARATUS FOR MEASURING FRACTURE TOUGHNESS OF A MATERIAL

BACKGROUND OF THE INVENTION

1. Field of the Invention

The invention relates to a method and an apparatus for measuring the fracture toughness of a material.

2. Description of the Prior Art

In order to characterize the damage resistance of a material and understand the particular characteristics of the material which are related to damage resistance, it is necessary to identify and measure the deformation resistance of the material. Such a general measure of deformation resistance is hardness.

Recent work has been directed to measurement of the material parameter, fracture toughness, using indentation techniques and includes a model that relates fracture toughness to the applied load and the length of radial cracks that emanate from an indentation, as described in A. G. Evans and E. A. Charles, J. Am. Ceram. Soc., 59:371, 1976.

Ceramists work to develop improved, higher toughness ceramics by modifying ceramic microstructure to result in improved toughness. This work demands a fracture toughness measurement sufficiently sensitive to allow reliable correlation between microstructure and measured fracture toughness. Fracture toughness data obtained using models that relate fracture toughness to applied load and radial crack length are highly empirical in nature and differences among the fracture toughness values obtained from the different models can be large. Such inconsistencies result from the many assumptions inherent in such models. One such assumption is that the response of the material being indented is volume conserving, which neglects phenomena such as ridge formation around indents in fully dense materials and crushing damage in porous materials. The nature of the surface of the material being indented and the ratio of the surface area being indented to the indented volume is another potential source of error, since models correlating applied load and radial crack length do not take into account friction between the surface of the material being indented and the indenter that strongly affects the stress state at the tip of a crack so-produced. Hence, it is difficult to obtain consistent and reliable measurements of the fracture toughness of a material using such models.

Conventional, prior art indentation based testing procedures, such as ASTM standards for fracture toughness testing, at best, provide estimates of the fracture toughness of the material. Moreover, R-curve testing involves measurements in the long crack regime which is outside the crack size regime appropriate for study of strength controlling flaws. Finally, indentation crack length-based measurements can only be used when a well-formed crack pattern, specifically four emanating cracks is formed in the material being tested.

Thus, there exists a need for a method and apparatus for direct measurement of the fracture toughness of a material, and, particularly, for ones for obtaining that data for cracks of dimensions comparable to naturally occurring flaws in the material being characterized. It is also desirable for the method to be usable with a wide variety of crack patterns.

SUMMARY OF THE INVENTION

The method and apparatus of the invention provide a direct measurement of the material fracture toughness from observation of the shape of a radial crack which emanates from an indent, without explicitly using the applied load in the analysis. The stress state at the crack tip is obtained by observing the crack shape, specifically, measuring the separation between the crack faces, the crack opening displacement (COD), as a function of distance from the crack tip. By computing crack shapes for loading boundary conditions appropriate to the indentation process using a finite element computational method, and measuring crack opening displacement as function of distance from the crack tip with high resolution microscopy, it is possible to generate high quality fracture toughness data. Furthermore, it is possible to create the indent and immediately perform microscopy in an isolated, controlled environment chamber that further enhances the quality of the fracture toughness data obtained.

Such a method and indentation apparatus are particularly useful for obtaining fracture toughness data for intrinsically brittle materials. Furthermore, the microscopic observation of the crack opening displacements demonstrate the ability of the material to resist crack propagation under load. Crack opening displacement data can be obtained from indentation induced cracks of dimensions chosen to mirror naturally occurring flaws in the material under study and, thus, allows accurate measurement of crack propagation resistance data in the same crack size regime appropriate to strength controlling flaws. Also, COD-based methods can be used with virtually any crack system and are not limited to crack systems of a particular geometry.

Another advantage of the crack opening displacement (COD)—based method of the invention is that it inherently provides a lower bound fracture toughness value. Since the COD-based method cannot over-predict the toughness of a material, it is an especially suitable characterization tool for design of safety critical components such as, for example, jet engine components. In COD-based measurements, the crack cannot have been opened to such an extent that the measured stress intensity factor exceeds the toughness value, since, if that were true, the crack would have continued to grow. Also, since the cracks observed in COD-based measurements are typically relatively small cracks, they do not develop toughening bridging or process zones which do develop in long-crack regime R-curve -based methods.

According to one aspect of the invention, a method for determining the fracture toughness of a material includes steps of (1) providing a material characterized by a fracture toughness; (2) indenting the material to produce an indented material including a crack characterized by a crack shape and wherein the crack shape is further characterized by a crack length, a crack tip, and a crack opening displacement; (3) examining the indented material microscopically to obtain a micrograph image of the crack shape and (4) measuring the crack opening displacement as a function of distance from the crack tip using the micrograph image to determine the fracture toughness.

Another aspect of the invention provides an apparatus for forming a crack in a sample for determining the fracture toughness of the sample including (1) a sample having a sample surface; (2) an indenter to produce a crack in the sample surface, pivotably translatable to allow observation of the crack; (3) a sample positioner to position the sample with respect to the indenter; and (4) a microscope to observe the crack.

Yet another aspect of the invention provides an apparatus for forming a crack in a sample for determining the fracture toughness of the sample including (1) a sample having a sample surface; (2) an indenter arm to produce a crack in the sample further including an indenter; (3) a sample positioner to position the sample at a desired height and orientation with respect to the indenter; and (4) a microscope to observe the crack.

BRIEF DESCRIPTION OF THE DRAWINGS

FIG. 1b is a cross-section of the indent of FIG. 1a.

DESCRIPTION OF PREFERRED EMBODIMENTS

Figure 1A:
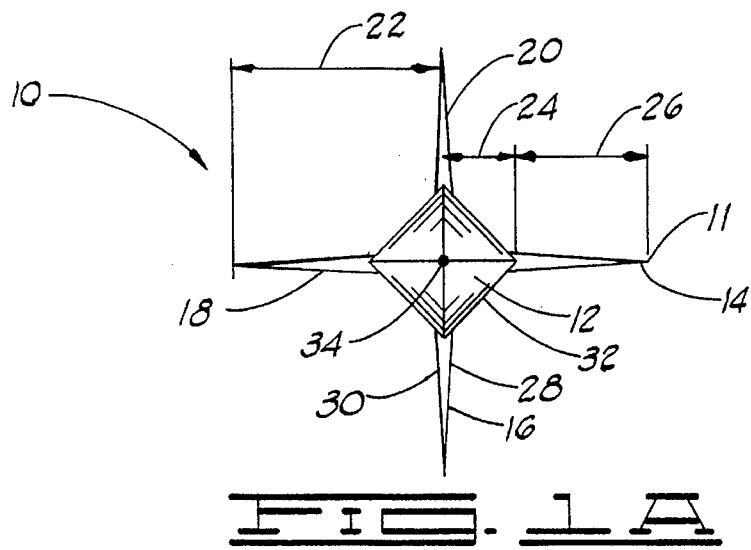
FIG. 1a is a schematic illustration of the geometry of an indent and crack pattern formed in a material.
Figure 1B:
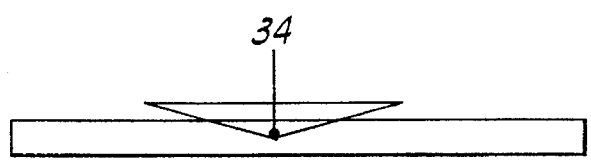

A method is provided for determining the fracture toughness of a material by forming an indent in the material to generate a crack. As used herein in the specification and claims, "fracture toughness" refers to a measure of a material's crack propagation resistance and is an engineering design parameter which relates the strength of a specific body with its largest internal flaw. Also, as used herein in the specification and claims, the term "indenting" refers to forming an "indent" through a process in which an applied load through sharp or pointed contact produces a surface impression and in some cases a system of surface cracks. Such an indent is shown schematically as indent 12 in the schematic indent and crack pattern 10 of FIG. 1. The material is then examined microscopically to obtain a micrograph image of the shape of the crack. Crack shape is described in terms of crack length and crack opening displacement. Referring to FIG. 1, four cracks 14, 16, 18, 20 emanate radially from indent 12 and form a radial crack pattern 10 with a specific Vickers type indenter geometry wherein line 22 is total crack length, the distance from crack tip 11 to the center of indent 12, as represented by the variable "a" in calculations which appear elsewhere in the specification. Line 24 is the distance between the center of indent 12 and edge 32 of indent 12, as represented by the variable "d" in calculations elsewhere in the specification. Line 26 is the distance between edge 32 and crack tip 11, as represented by the variable "c" elsewhere in the specification. Point 34 in FIGS. 1a and 1b indicates where a load is applied to create radial crack pattern 10. "Crack opening displacement" refers to the distance between crack faces 28 and 30 as shown in FIG. 1. Using micrograph image, which, for example, can be an SEM micrograph, crack opening displacement as a function of distance from the crack tip is measured and correlated with a solution for crack shape generated according to a finite element model to determine the fracture toughness of the material.

The foregoing method can be used for materials for which the ratio of the elastic modulus to the hardness parameter is greater than 10, and is preferably in the range of from about 1 to about 200, more preferably in the range of from about 5 to about 50 and most preferably in the range of from about 10 to about 30. Materials such as ceramics, composites, or metals in bulk specimen, such as a macroscopic three-dimensional "block" of material, or coating form can be characterized with the method. When the material undergoing testing is a coating or thin film, the coating or thin film thickness should be larger than the total length of a crack generated in the material by the indenting step. Ceramics that can be characterized using this method include materials such as $Si_3N_4$, $Al_2O_3$, MgO, Si, and $SiO_2$. Composites that can be characterized using this method include materials such as cermets with fine microstructure, whisker-reinforced metals, and whisker-reinforced ceramic matrix composites. Metals that can be characterized using this method include materials such as tungsten, hard materials like high carbon steel, heavily cold-worked metals, precipitation hardened steel, intermetallics such as $Ni_3Al$, and molybdenum carbides.

The step of indenting the material to form an indented material can further include steps of applying a load to the material followed by removing the load from the material.

Criteria for selecting loading for indentation will be discussed in greater detail together with theoretical considerations for determination of the fracture toughness of a material. Tables 1 and 2 show calculated loads and crack lengths for selected materials. As evident from Table 2, the minimum load needed to generate a particular crack system is material dependent. Highly brittle, low hardness, $H_v$, materials require small loads, while high toughness, low hardness materials require substantially higher loads. Loading conditions should be determined by first starting with a load at the low extreme of calculated loads, applying that load, observing the region surrounding the indent and repeating the procedure with successively higher loads until a desired crack pattern is generated, characterized by a crack of sufficient length for observation, at least 5 microns in length. Formation of a ring-like crack around the indent at a few multiples of the indentation dimension, known as a "lateral crack" is undesirable for performing a fracture toughness determination according to the method of the invention and indicates that a smaller load should be applied.

An additional step of preparing the surface of the material to reduce residual surface stress can also be performed. As used herein in the specification and claims "residual surface stress" refers to the state of stress of the material at the surface which is in general not stress free due to some amount of mechanical deformation associated with surface preparation. It is noted that the polishing and lapping procedures typically used to prepare a specimen for microscopy mechanically deform and, thus, alter the mechanical properties of the specimen surface layer. Hence, if the deformed surface layer is thick, i.e., equal in thickness to a substantial fraction, such as 1/10, of the indentation impression, the fracture toughness measured will be that of the mechanically altered layer and may not be representative of the bulk material. The thickness of an altered surface layer can be reduced by use of less damaging polishing techniques, such as polishing steps with less applied pressure, finishing with a finer grinding medium or the use of other final polishing steps such as an ion milling step to remove any damaged layer formed as a result of mechanical polishing steps.

The crack generated by the indenting step can be classified as a particular crack type, such as a radial or a median crack type, as known to one skilled in the art. A "median crack" refers to a well-formed half penny shaped surface crack and a "radial crack" refers to a more surface localized, shallow crack which is formed at lower applied indentation loads, and is also referred to as a "Palmqvist crack". The indenting step can generate one or more cracks. Crack length can be at least 5 microns and should be greater than any dimension of a microstructural feature of the material. For example, for a fiber-reinforced composite material, the length of the crack generated should be greater than the inter-fiber spacing to ensure that data obtained measures the properties of the fiber-matrix continuum.

The step of examining the indented material to ascertain crack shape can be performed at a resolution in the range of from about 1 to about 200,000, more preferably in the range of from about 100 to about 50,000, and most preferably in the range of from about 5 to about 20,000 using a microscope such as an optical microscope, an atomic force microscope, or a scanning electron microscope (SEM), which can be a field emission microscope. In order to obtain good quality SEM images of insulating samples, it is necessary first to coat the sample surface with a conductive material, such as gold, to prevent charging. It is not necessary to conductively coat insulating samples for examination in a field emission type scanning electron microscope, atomic force microscope, or optical microscope.

Crack opening displacement can be measured as a function of distance from the crack tip from the micrograph image using a micrometer. These measurements are then correlated with a crack shape calculated using finite element methods to determine the fracture toughness. Theoretical considerations useful for understanding this correlation relate to the kinematics of crack nucleation, connection of crack opening displacement to the crack tip stress field and the criticality of the stress field.

Radial cracks can be stably grown in a material by indenting the surface with a sharp indenter harder than the material to be tested. The sample of material must be at least several multiples of the crack depth, which is typically in the range of from about 10 microns to about 100 microns. During the indentation process, high Hertzian contact stresses develop beneath the indenter in the half space of material where irreversible deformation can occur under the high hydrostatic stresses, approximately equal to about 100 GPa, around the indenter contact area. Under sufficient applied load, stresses necessary for nucleation of subsurface cracks develop. The cracks form directly below the indenter and at the elastic/plastic boundary where maximum tensile stress occurs.

According to an analysis by Lawn and Swain, B. R. Lawn and M. V. Swain, J. Mater. Sci., 10:113, 1975, based on a simplified stress distribution beneath the indenter, the minimum load for nucleating a subsurface median crack, $P_c$, is given by:

$$P_c = \frac{34.67 K_c^4}{\phi^2 \theta^4 H_v^3}$$

where $\phi$ and $\theta$ are dimensionless proportionality constants relating the radius of the plastic zone to the indenter size and the hardness to yield strength, respectively. The parameters $\phi$ and $\theta$ are typically estimated at 1 and 0.2, respectively. $K_c$ and $H_v$ are, respectively, the material toughness and hardness. Table 1 shows the minimum loads and crack lengths for nucleation of cracks in some ceramics based on this analysis. Data are taken from I. J. McColm, *Ceramic Hardness*, Chapter 5, Plenum Press, New York, 1990.

TABLE 1

| Material | Fracture Toughness (MPa√m) | Hardness, $H_v$ | P* (N) | C* (microns) |
|---|---|---|---|---|
| Si | 0.700 | 10.600 | 0.004 | 0.200 |
| Soda Lime Glass | 0.750 | 5.600 | 0.040 | 0.800 |
| Alumino-Silicate Glass | 0.910 | 6.600 | 0.050 | 0.800 |
| Sapphire | 2.500 | 21.800 | 0.080 | 0.600 |
| Barium Titanate | 1.050 | 5.200 | 0.200 | 1.600 |
| SiC (NC203) | 4.000 | 24.000 | 0.400 | |
| Alumina (AD999) | 3.900 | 20.100 | 0.600 | 1.700 |
| Silicon Nitride NC132) | 4.000 | 18.500 | 0.900 | 2.000 |
| Corning Pyroceram (C9606) | 2.500 | 8.400 | 1.400 | 3.900 |
| ZrO (Ca stabilized) | 7.600 | 10.000 | 73.000 | 25.000 |
| WC | 12.000 | 13.200 | 198.000 | 36.000 |

The foregoing analysis can be refined further by incorporating the Boussinesq stress field solution as an approximation for the stresses under the indenter and values calculated using this refinement are shown in Table 2.

TABLE 2

| Material | Crack Type | Load (N) Predicted | Crack Length (microns) | Load (N) Observed | Crack Length (microns) |
|---|---|---|---|---|---|
| Soda-Lime Glass | Radial | 0.400 | 1.000 | | |
| | Median | 0.600 | 1.100 | 5.000 | 17.000 |
| | Lateral | 2.000 | 3.000 | | |
| Ge (Crystal) | Median | 0.014 | 0.160 | 0.020 | 0.250 |
| SiC (Polycrystal) | Radial | 5.000 | 3.000 | | |
| | Median | 14.000 | 4.000 | | |
| | Lateral | 40.000 | 7.000 | | |
| Si (Crystal) | Median | 0.050 | 0.360 | 0.030 | 0.650 |
| $Si_3N_4$ | Radial | 30.000 | 7.000 | | |
| | Median | 80.000 | 12.000 | | |
| | Lateral | 210.000 | 20.000 | | |
| Alumina | Median | 0.400 | 0.600 | 0.25–0.5 | 3.000 |

Close agreement is observed between predicted loads and crack lengths and experimentally observed loads that result in generation of median and radial cracks for Vickers indentations. Minimum load for crack generation depends upon the properties of the material being tested.

For a material exhibiting brittle behavior, the dominant deformation mode is elastic and crack opening displacement at any point on the crack surface, which can also be referred to as the crack shape, can be connected with the stress intensity using finite element techniques, given the loading boundary conditions. The stress intensity for loading, $K_I$, appropriate for the indentation process is given by:

$$K_I = \frac{E \Delta V(r)}{F(r) \sqrt{a}}$$

where $\Delta V(r)$ is the distance between the crack faces at a distance r from the crack tip, $F(r)$ is a non-dimensional shape factor, E is the Young's Modulus, and a is the total crack length from crack tip to center of indention.

FIGS., 2, 4, and 5 each show the shape factor F(r) with, respectively, data obtained for a soda lime glass, alumina single crystal and silicon single crystal.

Although the crack stress field from a neighboring crack will affect the crack opening displacement (COD) through stress amplification or relaxation, the fundamental connection between COD and the crack stress field was found to be unaffected based on finite element analysis. For example, for a case with four cracks present, absolute crack opening displacements were reduced due to stress relaxation associated with the additional cracks; however, the stress intensity, K, was proportionately reduced, thereby counteracting the crack opening displacement reduction. Hence, the foregoing analysis applies whether a single crack or multiple cracks are generated.

Crack opening displacements are connected to fracture toughness, which can also be described as crack propagation resistance, by consideration of the stress intensity. Upon removal of the load which generates the crack pattern, the stress intensity is at a critical level for impending crack propagation, that is, $K=K_c$. Considerable evidence, including experimental observations, supports this assumption and it can be expected to be valid for materials, such as brittle materials, where the ratio of the elastic modulus to the hardness parameter is large, greater than or equal to 10.

Normalized crack shapes have been calculated using finite element methods and analytical solutions for similar geometrical boundary conditions.

Figure 2:
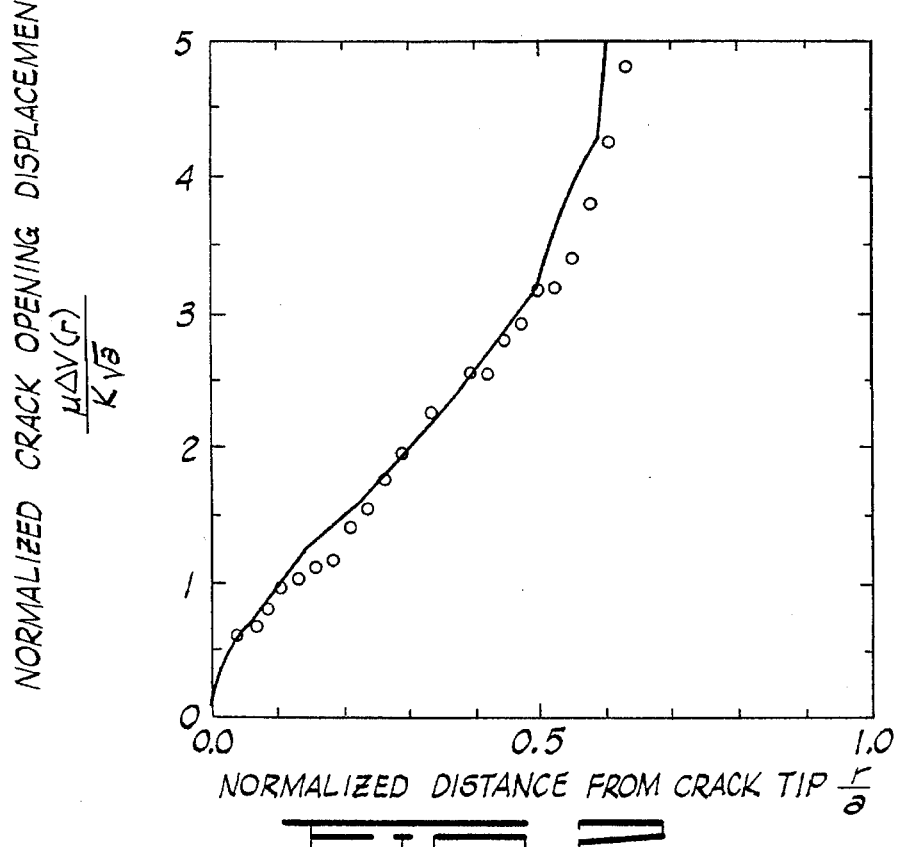
FIG. 2 is a graph showing calculated and observed normalized crack opening displacement as a function of normalized distance from crack tip in soda lime glass.
Figure 4:
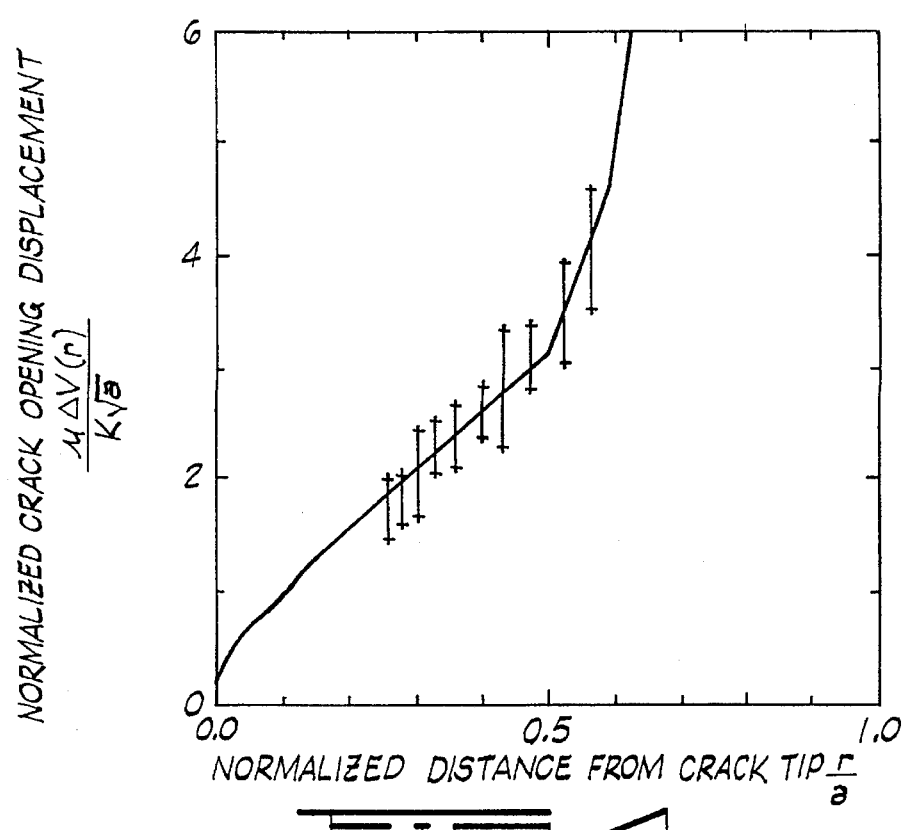
FIG. 4 a graph showing calculated and observed normalized crack opening displacement as a function of normalized distance from crack tip in an alumina single crystal.
Figure 5:
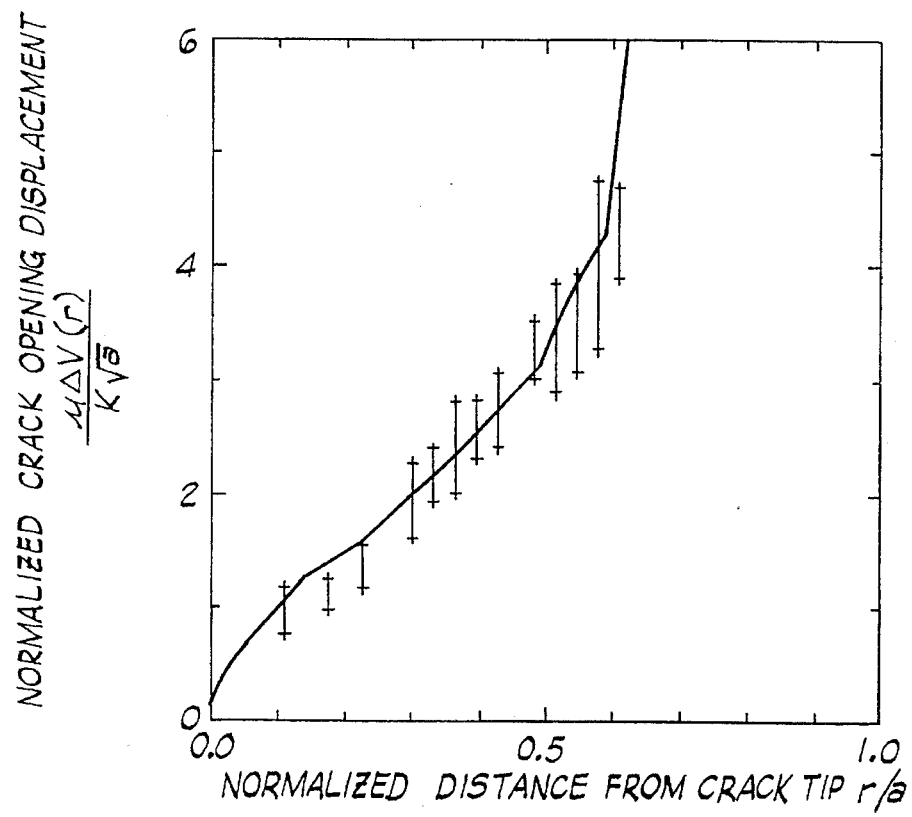
FIG. 5 a graph showing calculated and observed normalized crack opening displacement as a function of normalized distance from crack tip in a silicon single crystal.

A linear elastic solution was generated for a two dimensional crack in an infinite medium with the finite element computer code ABAQUS. The resulting non-dimensionalized crack opening displacement shape is shown in FIGS. 2, 4, and 5. Since the results are dimensionless, data for different materials will fall on the same calculated crack shape.

Figure 3:
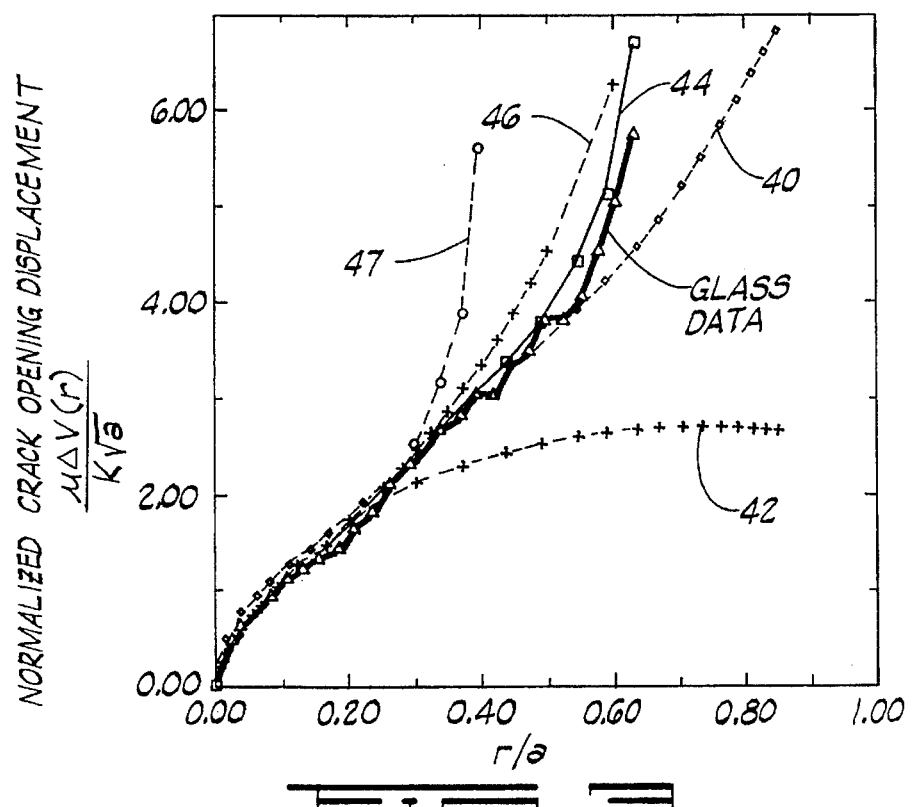
FIG. 3 is a graph showing calculated normalized crack opening displacement as a function of normalized distance from crack tip for various loading schemes plotted with data obtained for soda lime glass.

Four different loading schemes are considered and the calculated results are shown in FIG. 3. Curve 40 in FIG. 3 is generated for the case where the load from the residual stress field is applied at the center of the indentation as a concentrated load so that $d<<c$, as defined with respect to FIG. 1 i.e., for a center-loaded point force. Curve 42 in FIG. 3 is generated for the case where the load is distributed equally over the width, d, as defined with respect to FIG. 1, of the indent, i.e., for uniform internal pressure over the portion of the crack representing the indentation impression. Curve 44 in FIG. 3 is for the loading scheme wherein the concentrated load is applied at the edge of the indent, i.e., for point loading symmetric about the impression. As shown in FIG. 3, experimental data for a soda lime glass where $c/a=0.65$ fit curve 44 for the edge loading scheme. Curve 46 is the shape calculated for a 3-D center loaded fully imbedded penny shaped crack for which $c/a=0.35$, with c and a defined according to FIG. 1. Curve 47 is for point loading at $c/a=0.40$.

While it is recognized that a solution for a two dimensional crack fails to account for the three-dimensionality of actual cracks, it is noted that experimental data fit the two dimensional curve 44. This result can be explained by the fact that the tensile stress field that dominates crack growth during unloading is highly localized to the surface, so that the final configuration after load removal is a thin surface layer under tension, which is well-approximated by the two dimensional solution.

An apparatus is provided for forming a crack in a sample that can be used in subsequent fracture toughness determinations. The apparatus includes a sample having a sample surface, an indenter to crack the sample surface that pivots away from the sample surface after forming the crack to allow in-situ observation of the crack formed, a sample positioner to position the sample with respect to the indenter and a microscope to observe the crack.

The apparatus can further include a controller and actuator assembly to automatically raise and pivotably translate the indenter away from the sample surface to allow for observation of the crack. A transducer can be used to raise the indenter above the sample surface.

The indenter can also include fixed weights to provide a load for forming the crack and a Vickers-type diamond stylus for transferring the load to the sample surface. Vickers-type indentation measurements are commonly used in the art of materials mechanical property testing and a Vickers-type diamond stylus is an instrument component well-known to one skilled in the art.

The apparatus can further include an environmental chamber for providing a controlled environment for the sample that can be selected according to the particular properties of the material being tested, including avoidance of sample chemical reactivity with atmospheric oxygen and/or water vapor.

The microscope can have a resolution in the range of from about 5 nm to about 1 mm.

An apparatus is provided for forming a crack in a sample that can be used in subsequent fracture toughness determinations. The apparatus includes a sample having a sample surface, an indenter arm including an indenter to crack the sample surface, a sample positioner to position the sample at a desired height and orientation with respect to the indenter and a microscope to observe the crack. As used herein in the specification and claims, "orientation" refers to the angle that any preferred orientation in the sample makes with the indentation symmetry, for example, cracks can be produced along a specific crystallographic direction.

The sample positioner can further include a support plate and a guide plate so that the sample surface is positioned at a desired height and orientation with respect to the indenter.

Figure 6:
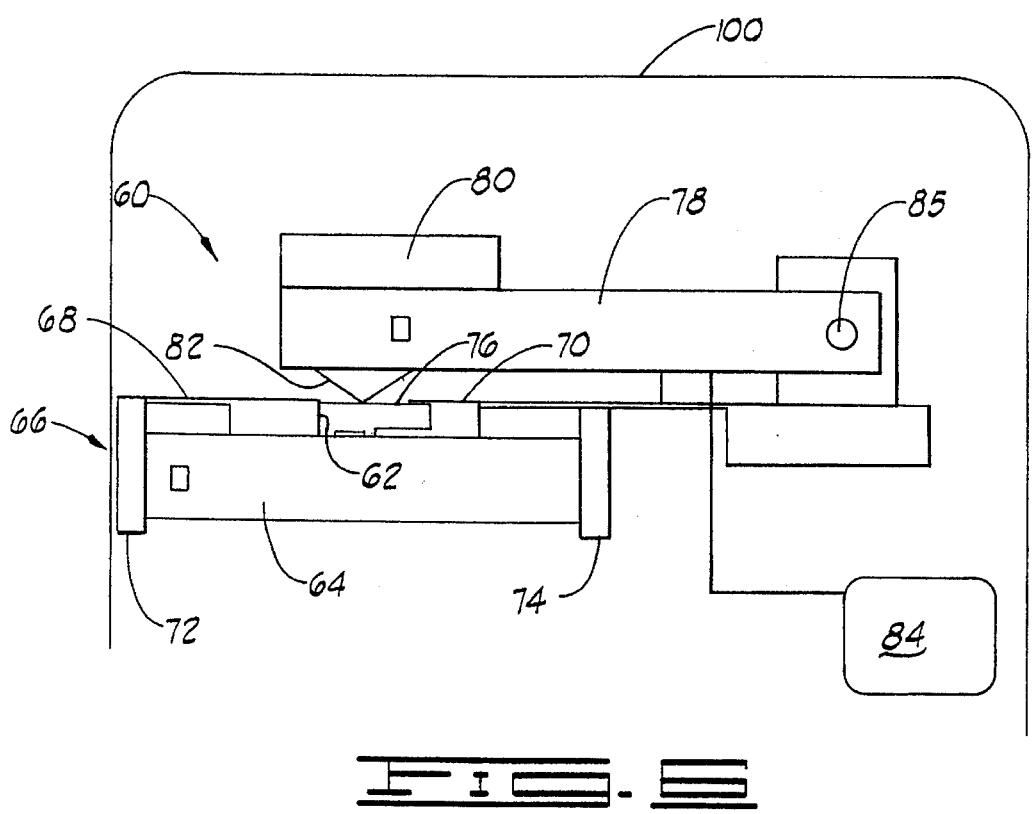
FIG. 6 is a schematic illustration in cross-section of an apparatus for forming a crack in a sample.

FIG. 6 is a schematic illustration in cross-section of an apparatus 60 for producing a crack in a test sample. Sample 62 rests on support plate 64, which can be a metal, ceramic or composite block, having sufficient rigidity to support sample 62 under load without bending and is held in place by height positioning jig 66. The support plate can be made from virtually any engineering material and, for example, can be made from a metal for ease of production and use. Height positioning jig 66 further includes holding tabs 68 and 70 attached to vertical supports 72 and 74. Height positioning jig 66 is slidably mounted over support plate 64 so that holding tabs 68 and 70 come to rest on surface 76 of sample 62 so that sample 62 is maintained at a selected, fixed height with respect to indenter arm 78, leaving a portion of surface 76 exposed. Holding tabs 68 and 70 exert sufficient pressure on sample 62 to prevent lateral motion of sample 62 with respect to support plate 64 during indenting. Height positioning jig 66 can be machined from materials such as stainless steel, high carbon steel, or aluminum which have appropriate mechanical properties to perform the foregoing functions.

A calibrated weight 80, whose mass is determined according to criteria already discussed in this specification, is attached to indenting arm 78 above indenter 82 to load indenter 82. Indenter 82 is made from a material harder than sample 62 and can be a Vickers-type diamond stylus or a Knoop indenter. Indenter arm 78 can be made of any material having appropriate mechanical properties to resist bending when loaded with weight 80. Apparatus 60 can be loaded into the chamber or stage where microscopy is performed.

Sample 62 can be indented automatically, and, optionally, remotely, using motor controller 84 and a stepping motor, not shown. The stepping motor drives arm positioning swivel 86 shown in the top view of FIG. 7 so that indenting arm 78 pivots in the direction shown by arrow 88 so that indenting arm 78 is positioned above sample 62. The swivel can be any reducing spur gear transmission or a worm gear driven by an axial motor. Indenter 82 is brought into contact with surface 76 of sample 62 using a vertical height adjustment transducer, not shown, which operates indenter arm vertical height adjuster 85 so that the load provided by weight 80 is transferred to surface 76. Vertical height adjuster 85 can be a hinge mechanism supported by a vertical actuator where, upon retraction, the hinged arm is free to descend to the surface, moderated in velocity by a viscous damping cell attached to the arm. For a typical indenting experiment, indenter 82 is kept in contact with surface 76 for a time in the range of from about 1 second to about 1 minute, with a time of about 10 seconds being typical. Once the indenting experiment is complete vertical height adjuster 85 raises indenter 82 above surface 76 and arm positioning swivel 86 rotates indenter arm 78 away from sample 62 so that the crack pattern generated by indenter 82 can be observed. If apparatus 60 is mounted within the vacuum chamber of an SEM, microscopy of the crack pattern can begin immediately, in-situ. If the apparatus is used with an optical microscope or an atomic force microscope (AFM), microscopy can also proceed immediately. Chemically reactive samples can be isolated and maintained within a controlled atmosphere in a controlled atmosphere chamber compatible with the microscope being used that also accommodates apparatus 60.

In order to further illustrate the present invention, the following example is provided. The particular compounds, processes and conditions utilized in the example are meant to be illustrative of the present invention and are not limited thereto.

EXAMPLE

The following example is provided to show the use of the method of the invention to determine the fracture toughnesses of three common materials, soda lime glass, silicon single crystal [110] fracture plane, and alpha-alumina single crystal [110]. The values thus obtained are compared with the generally accepted values for fracture toughnesses of these materials.

A sample of each of the three materials already-described was first polished flat so that no surface scratches were visible to the naked eye and coated with a standard microscopy gold coating to avoid charging of these insulating samples during scanning electron microscope (SEM) observation. Each sample was then indented to generate a crack pattern using a standard Vickers microhardness apparatus Leco model DM-400 loaded with in the range of from about a few grams to about several kilograms. The criteria for selection of loading for a particular material has been discussed in the Description of the Preferred Embodiments section of this specification. The load is held for 20 seconds, removed, and microscopy is then performed immediately in the SEM to generate a micrograph image of the crack pattern. Good quality micrograph images were obtained using a Hitachi single chamber, W filament at 25 kV SEM operated to result in a 20,000×magnification. A montage of images of the entire crack was obtained for each sample so that crack opening displacement (COD) data could be measured. A lower magnification SEM micrograph was also obtained for each sample for determination of the parameter "d", total crack length.

Figure 8:
FIG. 8 is a photomicrograph showing a crack opening for a measurement.

Crack opening displacements as a function of distance from crack tip were measured directly from the SEM micrographs for each sample at regular intervals along the crack path, i.e., at optimal locations where the crack faces were parallel with the overall crack orientation and where other surface features did not interfere with crack observation. An upper and lower bound were established for each COD measurement by taking a measurement, respectively, at the end of the region of the image Where contrast changes from that of the crack face to that of the surrounding bulk material and at the beginning of the region of the image contrast change. FIG. 8 is a photomicrograph that shows a crack opening for a measurement obtained from a Vickers indentation. COD measurements obtained at points along the crack path falling within the range of $r/a>0.2$ and $r/c<0.75$, where the parameters "a" and "c" are defined according to the foregoing discussion related to FIG. 1 and the parameter "r" represents the distance of the measurement point from the crack tip were selected for use in further analysis. Measurements taken at points neither too near the crack tip nor too near the indent yield the best results in calculation of fracture toughness. For points in the range of $r/a<0.2$, near the crack tip, crack opening displacements are too small for accurate measurement and points in the range $r/c>0.75$, near the indent, are influenced by their proximity to the indent.

The selected COD measurements obtained for each sample were then used to calculate multiple fracture toughness values using the earlier described formalism. The earlier described shape factor F(r) was determined from curve 44 in FIG. 3 which is generated for a center-loaded crack. The solution represented by curve 40 is material and crack length independent and, therefore, can be used for any combination of sample material, applied load and total crack length. FIGS. 2, 4, and 5, respectively, show COD data for soda lime glass, single crystal alumina and single crystal silicon superimposed on the calculated crack shape. The crack surface trace shapes agree qualitatively with the calculated shapes as can be seen from FIGS. 2, 4, and 5. The measured values for fracture toughness are summarized and compared with accepted values in Table 3. It is evident that they compare well with accepted literature values.

TABLE 3

| Material | Measured Fracture Toughness (MPa√m) | Reported Fracture Toughness (MPa√m) |
|---|---|---|
| Soda Lime Glass | 0.54 ± 0.025 | 0.40–0.80[1,2] |
| Si Single Crystal [110] | 0.84 ± 0.03 | 0.87 ± 0.04[1,2,3] |
| α-Alumina Single Crystal [110] | 2.48 ± 0.16 | 2.2–4.0[2] |
| NT154Si$_3$N$_4$[4] | 4.55 ± 0.25 | 4.85 ± 0.08[5] |

[1]M. F. Ashby and D. R. G. Jones, Engineering Materials: An Introduction to Their Properties and Applications, Pergamon Press, Elmsford, New York, 1981.
[2]I. J. McColm, Ceramic Hardness, Chapter 6, Plenum Press, New York, 1990.
[3]G. Michot, Fundamentals of Silicon Fracture, Crystal Properties & Preparation, Vols. 17 & 18 (1988), pp. 55–98, Trans. Tech. Publications, Switzerland.
[4]NT154 is a commercial silicon nitride manufactured by Norton Co., MA having a nominal composition 4 wt % Y$_2$O$_3$ and balance silicon nitride. Crack length = 55 mm. Longer cracks typically have larger toughness values due to R-curve behavior in this material.
[5]D. C. Salmon, PhD Thesis, Dept. Mech. Eng., University of Utah, 1992.

What is claimed is:

1. A method for determining the fracture toughness of a material comprising:

(1) providing a material characterized by a fracture toughness;

(2) indenting said material by applying a load with an indenter to produce an indented material including a crack characterized by a crack shape and wherein said crack shape is further characterized by a crack length, a crack tip, and a crack opening displacement;

(3) removing said load and said indenter from said material;

(4) examining said indented material microscopically to obtain a micrograph image of said crack shape; and using said micrograph image to determine said fracture toughness by utilizing a measurement of said crack opening displacement as a function of distance from said crack tip.

2. The method of claim 1 wherein said material is further characterized by an elastic modulus and by a hardness parameter and wherein the ratio of said elastic modulus to said hardness parameter is greater than 10.

3. The method of claim 2 wherein said ratio of said elastic modulus to said hardness parameter is in the range of from about 1 to about 200.

4. The method of claim 2 wherein said material is a material selected from the group consisting of ceramics, composites and metals.

5. The method of claim 1 wherein said material is a bulk specimen.

6. The method of claim 1 wherein said material is a coating.

7. The method of claim 1 wherein said step (2) of indenting said material further comprises steps of applying a load to said material followed by removing said load from said material.

8. The method of claim 7 wherein said crack is further characterized by a crack type and said load is chosen so that said crack type is selected from the group consisting of radial and median crack types.

9. The method of claim 1 wherein said crack is a single crack.

10. The method of claim 1 wherein said crack further includes at least two cracks.

11. The method of claim 1 wherein said material is further characterized by a material surface and said step (2) of indenting further includes a step of preparing said surface to reduce residual surface stress.

12. The method of claim 1 wherein said crack length is a at least 5 microns.

13. The method of claim 1 wherein said step (3) of examining said indented material is performed at a resolution in the range of from about 1 to about 200,000.

14. The method of claim 13 wherein said step (3) of examining said indented material is performed using a microscope selected from the group consisting of atomic force microscopes, optical microscopes, and scanning electron microscopes.

15. An apparatus for forming a crack in a sample for determining the fracture toughness of said sample comprising:

(1) a sample including a sample surface;

(2) an indenter to produce a crack in said sample surface and pivotably translatable to allow observation of said crack;

(3) a sample positioner to position said sample with respect to said indenter; and (4) a microscope to observe said crack.

16. The apparatus of claim 15 further including a controller and actuator assembly to automatically raise and pivotably translate said indenter away from said sample surface so that said crack can be observed.

17. The apparatus of claim 16 wherein said indenter further includes a transducer to raise said indenter above said sample surface.

18. The apparatus of claim 15 wherein said indenter further comprises a fixed weight to provide a load and a Vickers-type diamond stylus for transferring said load to said sample surface.

19. The apparatus of claim 15 further including an environmental chamber for providing a controlled environment for said sample.

20. The apparatus of claim 15 wherein said microscope is further characterized by a resolution and said resolution is in the range of from about 5 nm to about 1 mm.

21. An apparatus for forming a crack in a sample for determining the fracture toughness of said sample comprising:

(1) a sample including a sample surface;

(2) an indenter arm to produce a crack in said sample surface including an indenter said indenter arm being pivotally translatable to allow observation of said crack;

(3) a sample positioner to position said sample at a desired height and orientation with respect to said indenter;

(4) a microscope to observe said crack.

22. The apparatus of claim 21 wherein said sample positioner further includes a support plate and a guide plate and wherein said support plate positions said sample surface against said guide plate so that said sample surface is positioned at a desired height and orientation with respect to said indenter.

23. The apparatus of claim 21 wherein said indenter arm further comprises a fixed weight to provide a load and a Vickers-type diamond stylus for transferring said load to said sample surface.

24. The apparatus of claim 21 further including an environmental chamber for providing a controlled environment for said sample.

25. The apparatus of claim 21 wherein said microscope is further characterized by a resolution and said resolution is in the range of from about 5 nm to about 1 mm.

26. The method of claim 3 wherein said ratio of said elastic modulus to said hardness parameter is in the range of from about 5 to 50.

27. The method of claim 3 wherein said ratio of said elastic modulus to said hardness parameter is in the range of from about 10 to 30.

28. The method of claim 13 wherein said ratio of said elastic modulus to said hardness parameter is in the range of from about 100 to 50,000.

29. The method of claim 13 wherein said ratio of said elastic modulus to said hardness parameter is in the range of from about 5 to 20,000.

* * * * *

UNITED STATES PATENT AND TRADEMARK OFFICE
CERTIFICATE OF CORRECTION

Figure 7:
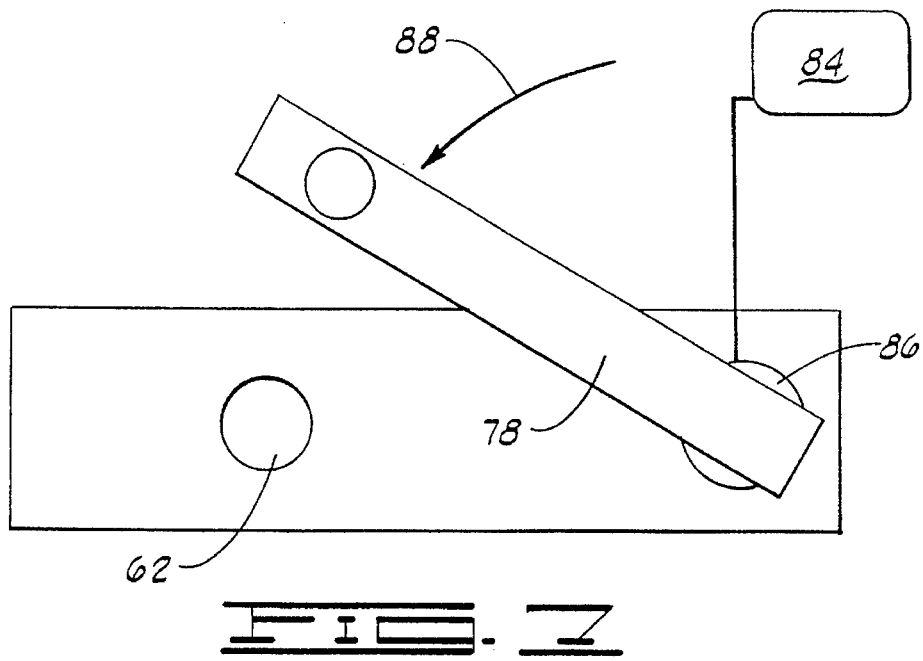
FIG. 7 is a schematic top view of an apparatus for forming a crack in a sample.
Figure 9:
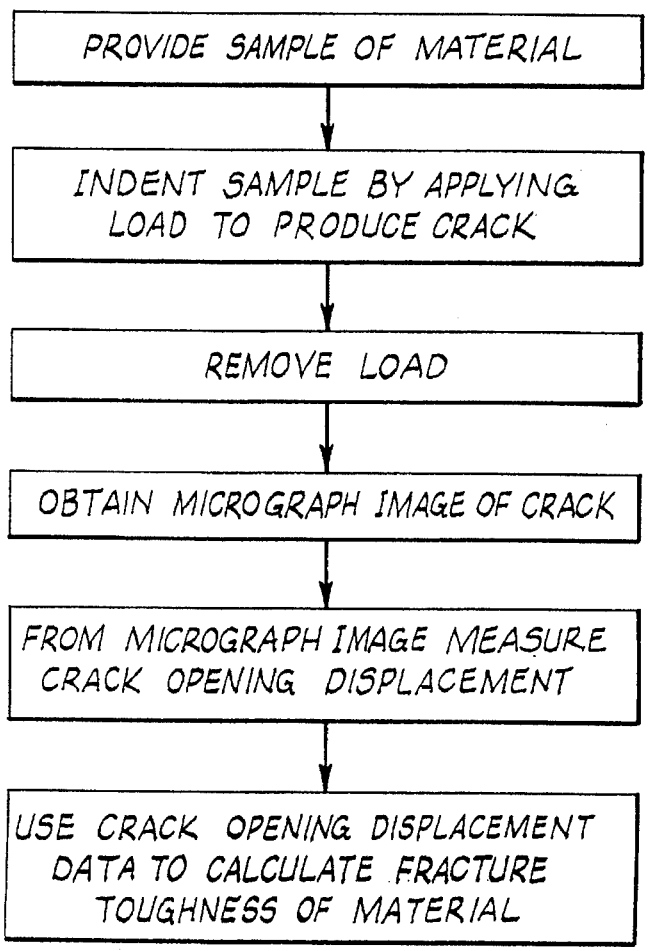

PATENT NO. : 5,602,329
DATED : February 11, 1997
INVENTOR(S) : Frederick G. Haubensak It is certified that error appears in the above-indentified patent and that said Letters Patent is hereby corrected as shown below:

Column 3, line 31: insert -- Fig. 9 is a flow chart summarizing steps included in the method of the invention. --
Column 8, line 34: after "sample.", insert -- Fig. 7 is a top view of the apparatus shown in Fig. 6.--
Column 9, line 24: after "chamber", insert -- such as bell jar 100--.
Column 12, claim 28, line 50-51: change "ratio of said elastic modulus to said hardness parameter" to --said resolution--.
Column 12, claim 29, line 53-54: change "ratio of said elastic modulus to said hardness parameter" to --said resolution--.

Signed and Sealed this

Twenty-sixth Day of August, 1997

BRUCE LEHMAN

Attest:

Attesting Officer

Commissioner of Patents and Trademarks